United States Patent
Kim et al.

(10) Patent No.: US 11,963,281 B2
(45) Date of Patent: Apr. 16, 2024

(54) LIGHTING DEVICE AND CONTROL METHOD THEREFOR

(71) Applicant: LUPLE INC., Seoul (KR)

(72) Inventors: Yong Duck Kim, Yongin-si (KR); Hyun Jun Park, Yongin-si (KR); Nam Su Lee, Seoul (KR)

(73) Assignee: LUPLE INC., Seoul (KR)

(*) Notice: Subject to any disclaimer, the term of this patent is extended or adjusted under 35 U.S.C. 154(b) by 0 days.

(21) Appl. No.: 17/928,220

(22) PCT Filed: May 26, 2021

(86) PCT No.: PCT/KR2021/095051
§ 371 (c)(1),
(2) Date: Nov. 28, 2022

(87) PCT Pub. No.: WO2021/242077
PCT Pub. Date: Dec. 2, 2021

(65) Prior Publication Data
US 2023/0225033 A1   Jul. 13, 2023

(30) Foreign Application Priority Data

May 29, 2020  (KR) ......................... 10-2020-0065274
Aug. 10, 2020  (KR) ......................... 10-2020-0099897

(51) Int. Cl.
| F21V 3/06 | (2018.01) |
| F21V 14/00 | (2018.01) |
| F21V 21/14 | (2006.01) |
| H05B 45/20 | (2020.01) |
| H05B 47/115 | (2020.01) |

(Continued)

(52) U.S. Cl.
CPC .......... *H05B 47/115* (2020.01); *F21V 3/0615* (2018.02); *F21V 14/00* (2013.01); *F21V 21/14* (2013.01); *H05B 45/20* (2020.01); *F21V 21/096* (2013.01); *G01B 7/023* (2013.01)

(58) Field of Classification Search
CPC ........ F21V 3/0615; F21V 14/00; F21V 21/14; F21V 21/096; H05B 45/20; G01B 7/023
See application file for complete search history.

(56) References Cited

U.S. PATENT DOCUMENTS

| 10,274,175 B1 * | 4/2019 | Wood ..................... G01D 5/145 |
| 10,465,892 B1 * | 11/2019 | Feinbloom ................ F21L 4/04 |
| 10,667,357 B1 * | 5/2020 | Feinbloom ............. H05B 45/10 |

(Continued)

FOREIGN PATENT DOCUMENTS

| JP | 2003187628 A | 7/2003 |
| JP | 2019064101 A | 4/2019 |

(Continued)

*Primary Examiner* — Evan P Dzierzynski
(74) *Attorney, Agent, or Firm* — Rabin & Berdo, P.C.

(57) ABSTRACT

The present invention relates to a lighting device and a control method therefor. The lighting device according to the present invention comprises: a light source unit comprising one or more light emitting elements; a first body to which the light source unit is mounted; a second body; a sensor unit for sensing at least one of a relative posture and a relative position of the first body to the second body; and a control unit for controlling the light emitting operation of the light source unit on the basis of at least one of the relative posture and the relative position of the first body.

15 Claims, 17 Drawing Sheets

(51) Int. Cl.
  *F21V 21/096*  (2006.01)
  *G01B 7/02*  (2006.01)

(56)  References Cited

U.S. PATENT DOCUMENTS

| | | | | |
|---|---|---|---|---|
| 2015/0035440 A1* | 2/2015 | Spero | ............... | F21S 41/147 |
| | | | | 315/153 |
| 2017/0090115 A1* | 3/2017 | Jurik | ............... | F21V 14/06 |
| 2018/0098399 A1* | 4/2018 | Takeshita | ............... | F21V 7/0008 |
| 2020/0072593 A1* | 3/2020 | Kobayashi | ............... | G01P 13/02 |
| 2020/0108162 A1* | 4/2020 | Rupnow | ............... | A61L 2/085 |
| 2021/0259070 A1* | 8/2021 | Boomgaarden | ............... | H05B 47/16 |

FOREIGN PATENT DOCUMENTS

| | | | |
|---|---|---|---|
| KR | 1020130001505 A | 1/2013 | |
| KR | 1020140006458 A | 1/2014 | |
| KR | 1020140147221 A | 12/2014 | |
| KR | 1020150012025 A | 2/2015 | |
| KR | 101524511 B1 | 6/2015 | |
| KR | 101687274 B1 | 12/2016 | |
| KR | 1020170053208 A | 5/2017 | |

* cited by examiner

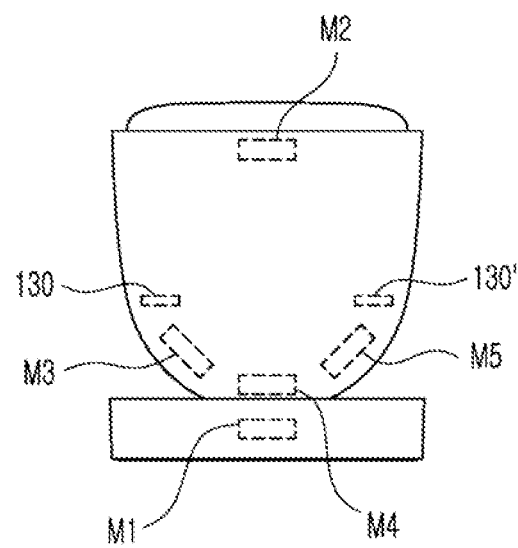
FIG. 14A
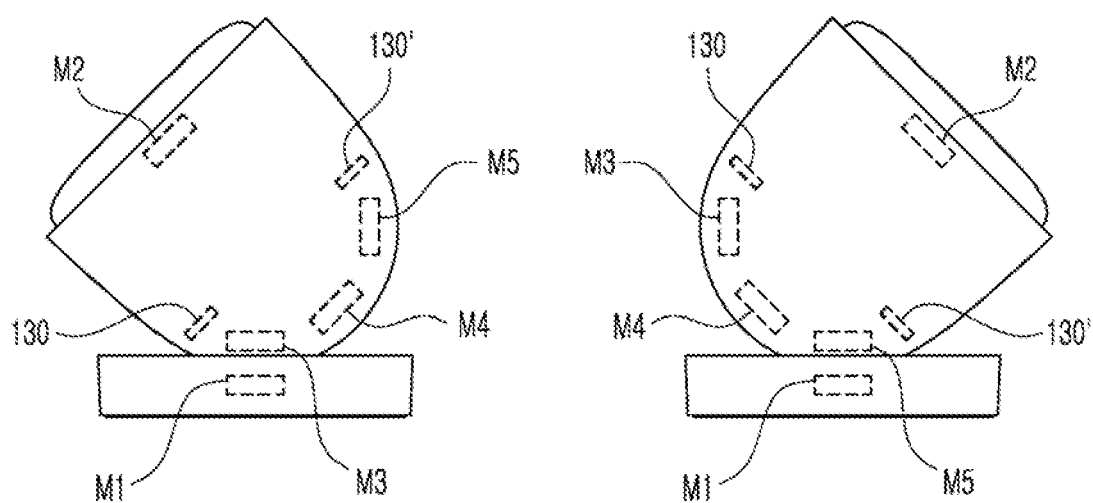
FIG. 14B
FIG. 14C

LIGHTING DEVICE AND CONTROL METHOD THEREFOR

TECHNICAL FIELD

The present invention relates to a lighting device and a control method thereof.

BACKGROUND ART

Lighting is becoming more important for modern people who spend most of their daily lives indoors. In addition, the development of artificial lighting gradually extends the time people engage in activities, and in particular, the number of people who work on night shifts, early morning deliveries, or the like is on the rise.

As indoor living expands and the number of people who work on night shifts increases, the population suffering from biorhythmic disturbances, sleep disorders, depression, and the like caused by the lack of exposure to sunlight increases. In order to resolve the issue, solutions configured to take care of the biorhythms through lighting are being introduced. However, the problem with the existing devices that provide care solutions for biorhythms is that the devices are large in size and cause photophobia when used.

DETAILED DESCRIPTION OF INVENTION

Technical Problem

A technical object of the present invention is to provide a portable and easy-to-operate lighting device and a method for controlling the same.

Technical Solution

As a technical means to achieve the objects described above, a lighting device according to the present invention includes a light source unit including one or more light emitting elements, a first body to which the light source unit is mounted, a second body, a sensor unit configured to sense at least one of a relative posture and a relative position of the first body to the second body, and a control unit configured to control the light emitting operation of the light source unit on the basis of at least one of the relative posture and the relative position of the first body.

The one or more light emitting elements may include one or more first light emitting elements emitting light having a first characteristic, and one or more second light emitting elements having a second characteristic.

The control unit may selectively turn on and off the one or more first light emitting elements and the one or more second light emitting elements on the basis of at least one of the relative posture and the relative position of the first body.

The first light emitting element may have a first spectrum, and the second light emitting element may have a second spectrum.

The first spectrum may have a greater light intensity in the wavelength band of 450 to 490 nm than in the other wavelength bands, and the second spectrum may have a lesser light intensity in the wavelength band of 450 to 490 nm than the first spectrum.

The second body may include a first magnetic material at a predetermined position, the sensor unit may include a magnetic sensor mounted at a predetermined position in the first body, and at least one of the relative posture and the relative position of the first body may be determined on the basis of a magnetic signal sensed at the magnetic sensor.

The first body may include an open upper portion, an inner space defined therein, and an outer circumferential surface with a gradually decreasing diameter in the downward direction.

The first body may include at least one of: a second magnetic material disposed in an upper center portion of the first body; a third magnetic material disposed in a lower portion of the first body at a predetermined distance from a central axis of the first body; and a fourth magnetic material disposed in a lower center portion of the first body.

The second body may include the first magnetic material in a center of the second body.

The first body and the second body may be coupled to each other by the magnetic force of the first magnetic material and the second magnetic material, with a lower portion of the second body and an upper portion of the first body facing each other.

With the first body being mounted on an upper portion of the second body, the first body may be fixed to the second body in an inclined posture at a predetermined angle by a magnetic force of the first magnetic material and the third magnetic material.

With the first body being mounted on the upper portion of the second body, the first body may be fixed to the second body in an upright posture by a magnetic force of the first magnetic material and the fourth magnetic material.

The magnetic sensor may be disposed in a lower portion of the first body at a predetermined distance from an upper portion of the third magnetic material.

With the first body being fixed to the second body in an inclined posture at a predetermined angle by the magnetic force of the first magnetic material and the third magnetic material, the magnetic sensor may be turned on by a magnetic field generated by the first magnetic material.

A support extending upward from the second body may be further included.

The first body may be tiltably coupled to the support.

The support may include a first support and a second support which extend upward from the second body.

A side of the first body may be tiltably coupled to the first support and the second support.

The support may protrude upward from a center of the second body, a spherical sphere may be formed at an end of the support, and the sphere may be rotatably inserted into an insertion hole formed in a lower portion of the first body so as to be rotated in three axes (roll/pitch/yaw).

The support may protrude upward from a center of the second body to be tiltably coupled to an inside of the first body, and a through slit may be formed in the first body through which the support may be passed.

The sensor unit may include an inertial sensor mounted in the first body to sense the posture and the movement of the first body, or a switch turned on and off according to the posture of the first body.

The first body may include an inner space defined therein, and an open upper portion.

The light source unit may include a plurality of light emitting elements arranged in the inner space at a predetermined distance from a central axis of the first body.

The lighting device may further include a main diffusion unit configured to cover the open upper portion of the first body and to diffusely transmit light generated by the light source unit.

The lighting device may further include an auxiliary diffusion unit disposed over the plurality of light emitting elements to diffusely transmit light generated by the plurality of light emitting elements to the main diffusion unit.

The auxiliary diffusion unit may include a lens including, formed on a lower portion thereof, a plurality of concave surfaces corresponding to each of the plurality of light emitting elements.

The auxiliary diffusion unit may include a plurality of lenses corresponding to each of the plurality of light emitting elements.

The plurality of lenses may have a concave surface formed on a lower portion or a convex surface formed on an upper portion.

A corrosion surface may be formed on at least one of a lower surface of the main diffusion unit and an upper surface of the auxiliary diffusion unit.

A magnetic material disposed in an upper center portion of the inner space defined in the first body may be further included.

The magnetic material may be positioned below the main diffusion unit, and at least a portion of the magnetic material may be positioned above the auxiliary diffusion unit.

The lighting device may further include a frame including a magnetic material insertion portion formed in the center to receive the magnetic material that is inserted and fixed therein; and a light emitting element mounting portion which is coupled to the frame such that the magnetic material is passed therethrough, and on which the plurality of light emitting elements are mounted.

The magnetic material may be positioned above the light emitting element mounting portion.

The magnetic material may be formed such that its upper portion is narrower in width than its lower portion.

A lighting device according to another embodiment of the present invention may include a light source unit including one or more light emitting elements, a first body to which the light source unit is mounted, a second body, a sensor unit configured to sense at least one of a relative posture and a relative position of the first body with respect to the second body, a camera unit mounted in the first body or the second body, and a control unit configured to control a light emitting operation of the light source unit on the basis of at least one of a relative posture and a relative position of the first body and an image captured by the camera unit.

The control unit may include a learning model configured to be inputted with an image captured by the camera unit and determine circumstances of a user, in which the control unit may adjust at least one of a color temperature, a brightness, and a color of light emitted from the light source unit according to the circumstances of the user determined by the learning model.

A method for controlling a lighting device according to the another embodiment of the present invention may include turning on a light source unit to generate light at a first brightness level, when an ON interrupt is generated while a light source unit is OFF, turning off the light source unit when an OFF interrupt is generated before a preset time elapses after the light source unit is turned on, turning off the light source unit when the preset time elapses after the light source unit is turned on, turning on the light source unit to generate light at a second brightness level, when the ON interrupt is generated while the light source unit is OFF by the OFF interrupt generated, and turning on the light source unit to generate light at the first brightness level, when the ON interrupt is generated while the light source unit is OFF after the preset time elapses.

A lighting device according to still another embodiment of the present invention may include a body, a light source unit mounted in the body to emit light to an upper portion of the body, a sensor unit mounted in the body to sense at least one of a posture and a movement of the body, and a control unit configured to control a light emitting operation of the light source unit on the basis of at least one of the posture and the movement of the body.

The lighting device may further include a cover part detachably coupled to the upper portion of the body, and a cover coupling sense unit configured to sense whether or not the cover part is coupled to the upper portion of the body.

The control unit may not turn on the light source unit when the cover part is coupled to the upper portion of the body.

The cover coupling sensing unit may include at least one of a magnetic sensor configured to sense a magnetic material mounted in the cover part, an illuminance sensor configured to sense illuminance of the upper portion of the body, and a physical switch that is pressed when the cover part is coupled to the upper portion of the body.

Effects of Invention

According to the present invention, a portable and easy-to-operate lighting device that takes care of the biorhythms and a method for controlling the device can be provided.

BRIEF DESCRIPTION OF DRAWINGS

FIGS. 14A, 14B, 14C are diagrams illustrating relative positions of a magnetic material and a magnetic sensor according to postures and positions of a first body and a second body according to another embodiment of the present invention.

MODE FOR EMBODYING INVENTION

Figure 1:
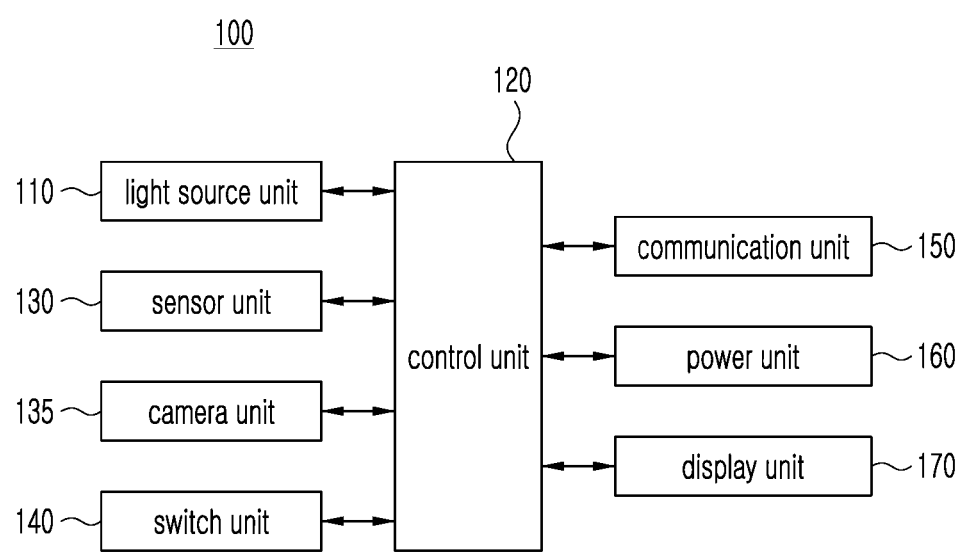
FIG. 1 is a block diagram schematically illustrating a configuration of a lighting device according to an embodiment of the present invention.

Hereinafter, preferred embodiments of the present invention will be described in detail with reference to the accompanying drawings so that those with ordinary knowledge in the art can easily achieve the present invention. However, it will be understood that the present invention can be implemented in various other different forms and should not be construed as being limited to certain embodiments described herein. In the following description, parts that are irrelevant to the present invention are omitted for the purpose of clear description of the disclosure, and the same or similar elements are denoted with the same or similar reference numerals throughout the description.

FIG. 1 is a block diagram schematically illustrating a configuration of a lighting device according to an embodiment of the present invention.

Referring to FIG. 1, a lighting device 100 may include a light source unit 110, a control unit 120, a sensor unit 130, a camera unit 135, a switch unit 140, a communication unit 150, a power supply unit 160, and a display unit 170. Of course, the lighting device 100 may not include the sensor unit 130, the camera unit 135, the switch unit 140, the communication unit 150, and the display unit 170 according to embodiments.

The light source unit 110 may include one or more light emitting elements for emitting light, such as a light emitting diode (LED), an organic light emitting diode (OLED), and the like, in which the light source unit 110 may emit light while operating under the control of the control unit 120.

The light emitting element may be implemented with an LED, an OLED, and the like, which is manufactured to emit light having a spectrum with a strengthened or weakened specific wavelength band that affects the hormone secretion of a user.

Figure 2A:
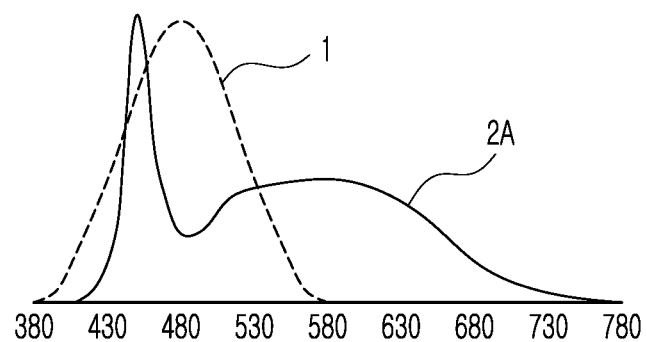
FIGS. 2A, 2B, and 2B are diagrams illustrating a light emission spectrum of a light emitting element according to an embodiment of the present invention.
Figure 2B:
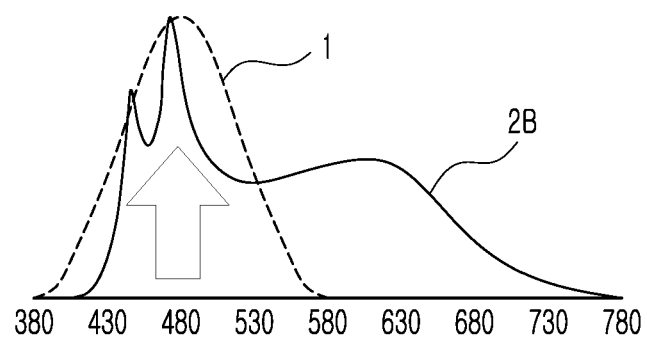
Figure 2C:
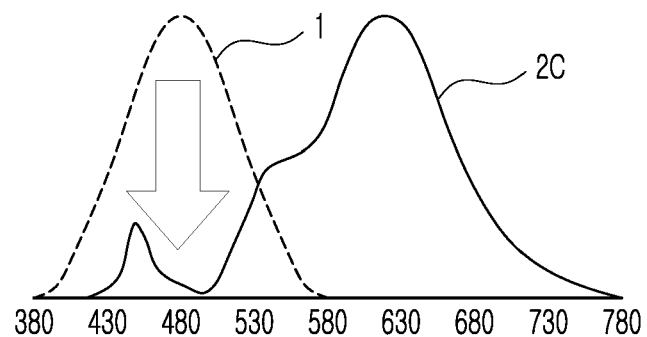

FIGS. 2A, 2B, and 2C are diagrams illustrating a light emission spectrum for each type of light emitting element.

Referring to FIGS. 2A, 2B, and 2C, when light is decomposed and arranged according to wavelengths, a region 1 having a parabolic shape centered on a wavelength of 460 to 480 nm may be referred to as a melanopic sensitivity region. By the way, in the case of humans, it is known that the melatonin hormone is regulated by the amount of light that enters through the eyes in the wavelength band of a melanopic region. Melatonin is a biological hormone secreted in the brain and affects the body's wakefulness, relaxation, or sleep. The human body activates the body by minimizing the amount of melatonin secretion during the day when there is a lot of sunlight and gets a deep sleep during the night through melatonin secretion.

FIG. 2A illustrates the light emission spectrum of a normal white LED.

FIG. 2B illustrates the light emission spectrum of an awakening LED. The awakening LED is a light emitting element, similar to sunlight, implemented to have a light emission spectrum in which the light intensity in the wavelength band of 450 to 490 nm is greater than in other wavelength bands. Use of the lighting device 100 to which the awakening LED is applied may help activate the body and improve concentration by minimizing melatonin secretion.

FIG. 2C illustrates the light emission spectrum of a relaxation LED. The relaxation LED is a light emitting element implemented to have a light emission spectrum in which the light intensity in the wavelength band of 450 to 490 nm is attenuated compared to the light emission spectrum of the awakening LED (or general white LED). Use of the lighting device 100 to which the relaxation LED is applied may relax the body, and help to have a rest and a deep sleep by increasing melatonin secretion.

According to an embodiment, both the relaxation LED and the awakening LED may be applied to the lighting device 100, or either of the two may be applied. In addition, according to an embodiment, only the general white LED may be applied to the lighting device 100, or other types of light emitting elements may be applied.

Referring back to FIG. 1, in addition to the examples shown in FIGS. 2A, 2B, and 2C, the light source unit 110 may be implemented using a light emitting element emitting light having a light emission spectrum determined according to the purpose of use of the lighting device 100. Designing the light emitting elements such as LEDs and OLEDs so that light of a specific light emission spectrum is emitted is already well known, and thus detailed description thereof is omitted.

The control unit 120 may control the overall operation of the lighting device 100. The control unit 120 may control the light emitting operation of the light source unit 110.

The control unit 120 may control the light emitting operation of the light source unit 110 according to information or signals detected at the sensor unit 130. In addition, the control unit 120 may be implemented to control the light emitting operation of the light source unit 110 according to the user's manipulation on a switch. In addition, the control unit 120 may be implemented to control the light emitting operation of the light source unit 110 according to a control signal or information inputted from an external device through the communication unit 160.

On the other hand, when the lighting device 100 includes the camera unit 135, the control unit 120 may control the light emitting operation of the light source unit 110 on the basis of an image captured by the camera unit 135. To this end, the control unit 120 may include a learning model configured to receive an image captured by the camera unit 135 and determine a situation the user is in. In addition, the control unit 120 may adjust at least one of color temperature, brightness, and color of the light emitted from the light source unit 110 according to the user situation determined by the learning model.

The control unit 120 may be implemented as a processor, a controller, an arithmetic logic unit (ALU), a digital signal processor, a microcomputer, a field programmable gate array (FPGA), a programmable logic unit (PLU), a microprocessor, and the like.

The sensor unit 130 may include at least one of various types of sensors such as an infrared sensor, a distance sensor, a gyroscope sensor, a gravity sensor, a position sensor, a proximity sensor, an illuminance sensor or an RGB sensor, a magnetic sensor, an inertial sensor, a touch sensor, a microphone, or the like. For example, the sensor unit 130 may sense a posture and a position of the lighting device 100, the surrounding environment of the lighting device 100, or a user's motion.

The camera unit 135 may capture images of the surroundings of the lighting device 100. The user may be included in the image captured by the camera unit 135.

The switch unit 140 may include a physical switch such as a push button switch, a toggle switch, a slide switch, and the like.

The communication unit 150 may include a communication module such as a Bluetooth communication module, a Bluetooth Low Energy (BLE) communication module, a near field communication unit, a WLAN (Wi-Fi) communication module, a Zigbee communication module, an infrared (IrDA, infrared Data Association)) communication module, a Wi-Fi Direct (WFD) communication module, an ultra-wideband (UWB) communication module, an Ant+ communication module, and the like.

The lighting device 100 may receive a control command or various information relating to the operation of the lighting device from a user terminal (not illustrated) such as a smart phone through the communication unit 150, or may provide state information and operation information of the lighting device 100 or information collected by the lighting device 100 to the user terminal.

The power supply unit 160 supplies the operating power of the lighting device 100. The power supply unit 160 may be implemented as a secondary battery that can be recharged when discharged so as to be repeatedly used. The secondary battery may be a lead-acid battery, a nickel-cadmium battery (NiCd), a nickel-metal hydride battery (Ni—MH), a lithium-ion battery (Li-ion), a lithium-ion polymer battery (Li-ion polymer), or the like. Of course, the power supply unit 160 may be implemented as a disposable battery according to an embodiment. On the other hand, the battery of the power supply unit 160 may be implemented to be charged through a power cable (not illustrated) or may be implemented to be charged through wireless charging.

The display unit 170 may display state information of the lighting device 100 to the outside. For example, the charging states of the battery of the lighting device 100 may be displayed and distinguished in colors. Of course, it may also be configured to display various information relating to the operation of the lighting device 100, lighting time, lighting mode, current time, timer, and the like.

Figure 3:
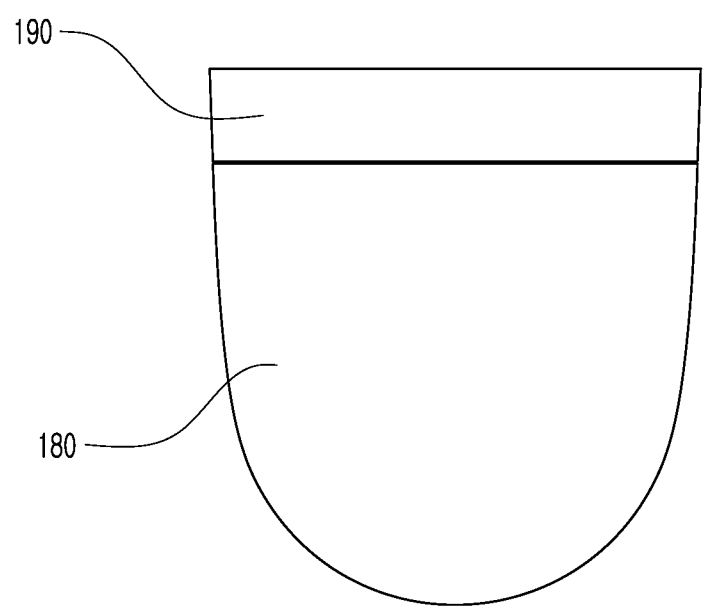
FIG. 3 is a diagram illustrating an external form of a lighting device according to an embodiment of the present invention.
Figure 4:
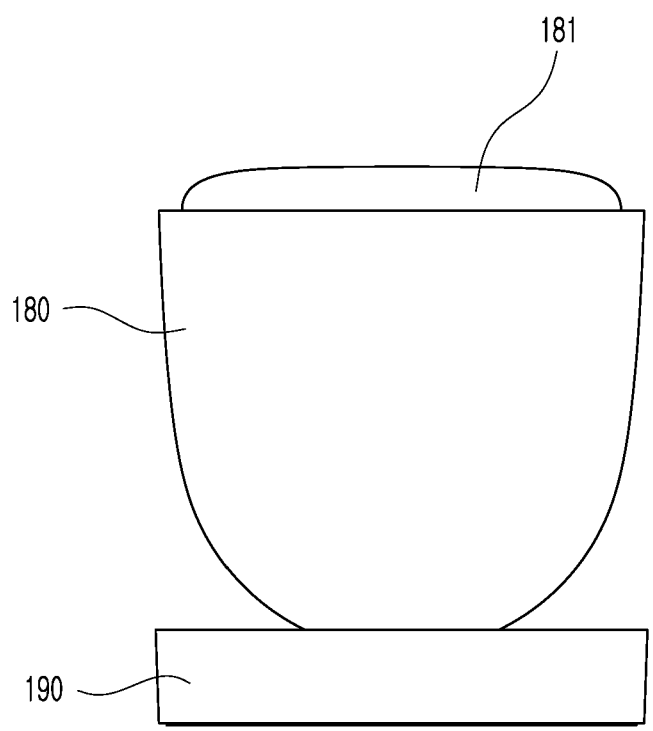
FIG. 4 is a diagram illustrating an external form of a lighting device according to an embodiment of the present invention.
Figure 5:
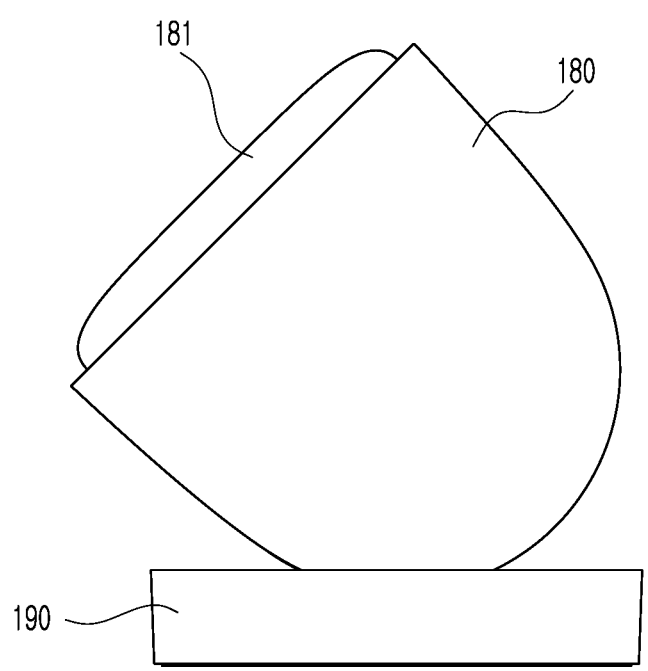
FIG. 5 is a diagram illustrating an external form of a lighting device according to an embodiment of the present invention.

FIGS. 3 to 5 are diagrams illustrating an external form of a lighting device according to an embodiment of the present invention.

Referring to FIGS. 3 to 5, the lighting device 100 may further include a first body 180, a second body 190, and a main diffusion unit 181.

The first body 180 may be implemented in a form having an inner space defined therein and an open upper portion. The light source unit 110, the control unit 120, the sensor unit 130, the switch unit 140, the communication unit 150, and the power supply unit 160 described in FIG. 1 may be mounted in the inner space of the first body 180.

The second body 190 may serve as a cover protecting the main diffusion unit 181 exposed to the outside of the first body 180. In addition, the second body 190 may also serve as a support on which the first body 180 is mounted when the lighting device 100 is used.

The main diffusion unit 181 may cover the open upper portion of the first body 180 and diffusely transmit the light generated by the light source unit 110. The main diffusion unit 181 may be implemented with a translucent material that diffusely transmits light to a certain level. As a result, the main diffusion unit 181 may transmit light to the outside, but the inside of the first body 180 may be made invisible from the outside. The main diffusion unit 181 may diffuse light using a synthetic resin material such as light-diffusing polycarbonate (PC) or light-diffusing film.

On the other hand, the main diffusion unit 181 may also be implemented as a smart mirror that changes the transmittance using an electrochromic element.

Referring to FIG. 3, when the lighting device 100 is not in use, with a lower portion of the second body 190 and an upper portion of the first body 180 facing each other, the first body 180 and the second body 190 may be coupled to each other.

The first body 180 and the second body 190 may be coupled to each other by the magnetic force of magnetic materials (not illustrated) respectively disposed therein. Of course, according to an embodiment, a side of one of the first body 180 and the second body 190 may be fitted into a side of the other by physical pressure, or threads may be formed on both sides for screw-coupling with each other.

Referring to FIGS. 4 and 5, to use the lighting device 100, the first body 180 and the second body 190 may be separated, and then the first body 180 may be mounted on the second body 190.

As illustrated in FIG. 4, the first body 180 may be fixed in an upright posture on the second body 190. In addition, as illustrated in FIG. 5, the first body 180 may be fixed in an inclined posture at a predetermined angle on the second body 190.

The first body 180 may be fixed to the upper portion of the second body 190 in the postures as illustrated in FIGS. 4 and 5, by the magnetic force of the magnetic materials (not illustrated) disposed in the first body 180 and the second body 190.

Figure 6:
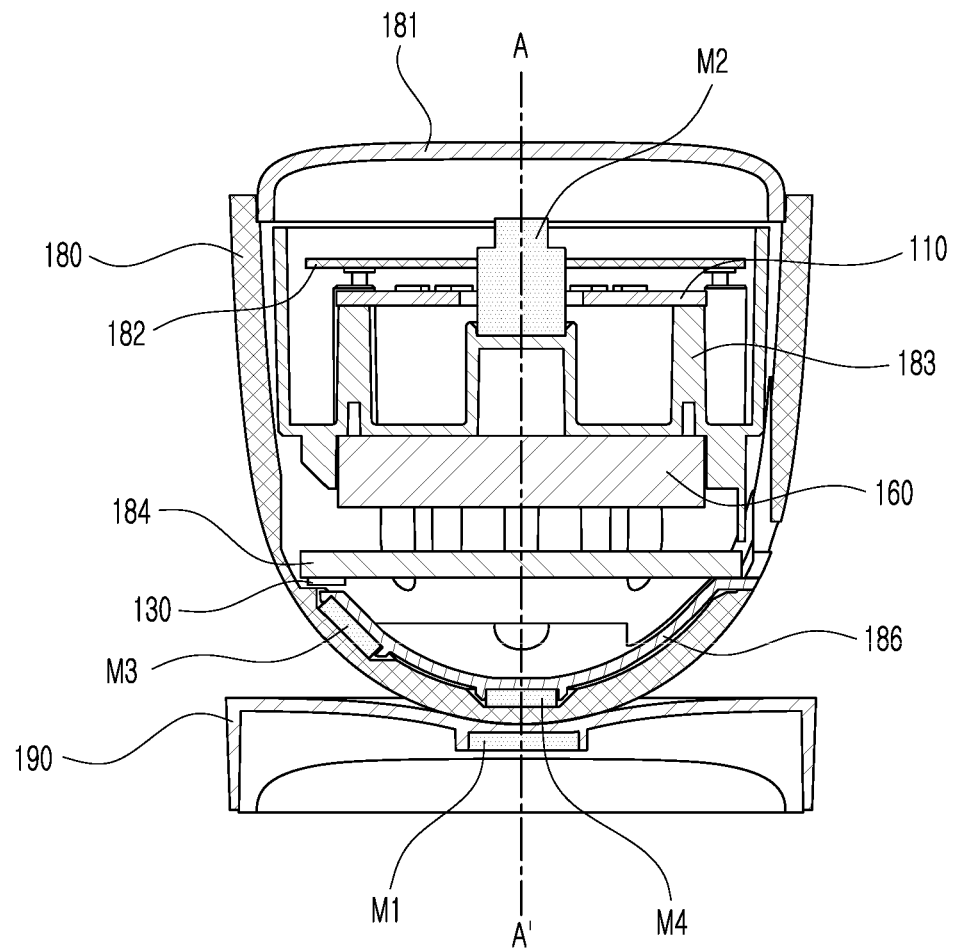
FIG. 6 is a cross-sectional view illustrating an internal configuration of a lighting device according to an embodiment of the present invention.

FIG. 6 is a cross-sectional view illustrating an internal configuration of the lighting device according to an embodiment of the present invention.

Referring to FIG. 6, the first body 180 may be implemented in such a shape that it has an open upper portion, an inner space, and an outer circumferential surface with a gradually decreasing diameter in the downward direction. The first body 180 may be implemented with a material such as synthetic resin having a strength greater than or equal to a certain level.

The inner space of the first body 180 may include, disposed therein, second to fourth magnetic materials M2, M3, and M4, an auxiliary diffusion unit 182, the light source unit 110, a frame 183, the sensor unit 130, a main board 184, and the like.

A first magnetic material M1 may be provided inside the second body 190. The first magnetic material M1 may be disposed in the center of the second body 190.

The first to fourth magnetic materials M1, M2, M3, and M4 may be magnets or magnetic materials such as iron, nickel, cobalt, or the like.

Figure 7:
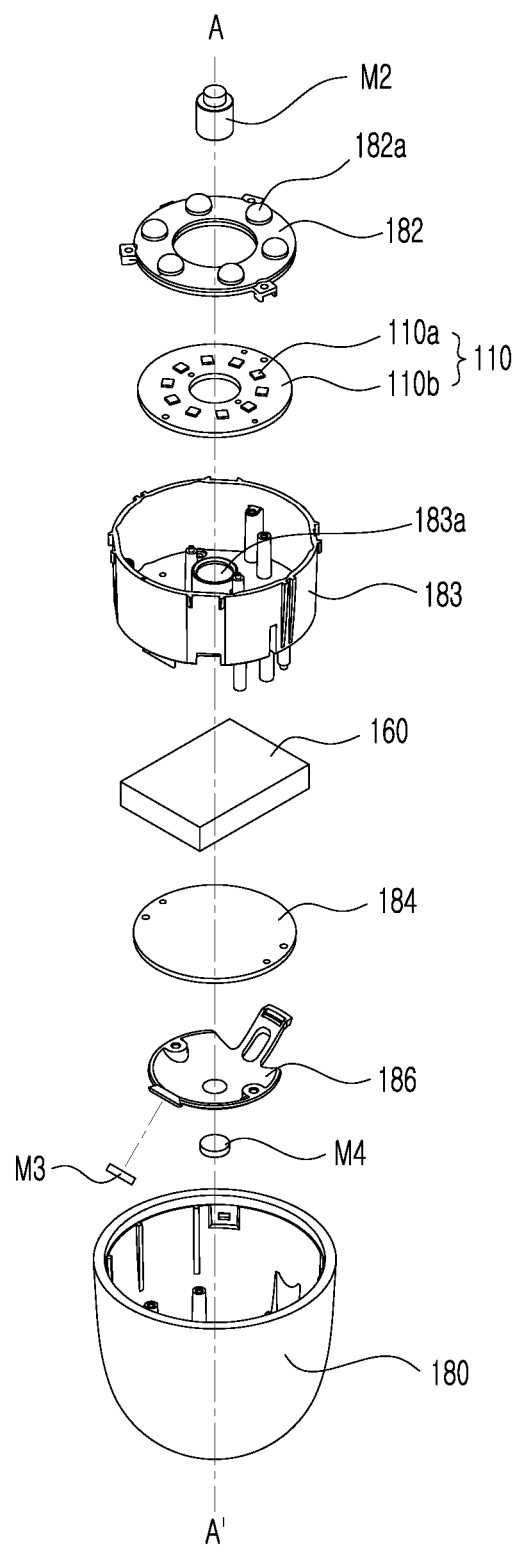
FIG. 7 is an exploded view illustrating components disposed inside a first body according to an embodiment of the present invention.

FIG. 7 is an exploded view illustrating components disposed inside the first body according to an embodiment of the present invention.

Referring to FIGS. 6 and 7, the second magnetic material M2 may be disposed in the upper center portion of the first body 180. The third magnetic material M3 may be disposed on a lower side of the first body 180 at a predetermined distance from a central axis AA' of the first body 180. The fourth magnetic material M4 may be disposed in a lower center portion of the first body 180.

The sensor unit 130 may be implemented as a magnetic sensor such as a Hall sensor. The sensor unit 130 may be mounted in a predetermined position inside the first body 180 to sense at least one of a relative posture and a relative position of the first body 180 with respect to the second body 190.

For example, the sensor unit 130 may be disposed in a position such that the sensor unit 130 is turned on by the first magnetic material M1 when the first body 180 is in a specific posture and/or position relative to the second body 190, without being affected by the magnetic field generated by the second to fourth magnetic materials M2, M3, and M4. For example, as illustrated in FIG. 6, the sensor unit 130 may be disposed on a lower side of the first body 180 at a predetermined distance from the upper portion of the third magnetic material M3 so as not to be affected by the magnetic field generated by the second to fourth magnetic materials M2, M3, and M4. In addition, the sensor 130 may be implemented so as to be turned on upon sensing a magnetic signal of the first magnetic material M1 as the first body 180 is fixed to the second body 190 in an inclined posture as illustrated in FIG. 5.

The control unit 120 may control the light emitting operation of the light source unit 110 on the basis of at least one of the relative posture and the relative position of the first body 180 with respect to the second body 190. In addition, the control unit 120 may selectively turn on and off different types of light emitting elements on the basis of at least one of the relative posture and the relative position of the first body 180 with respect to the second body 190.

On the other hand, when the proximity between the plurality of light emitting elements 110*a* and the main diffusion unit 181 makes it difficult to achieve uniform illumination on the entire surface of the main diffusion unit 181, the auxiliary diffusion unit 182 may be provided between the plurality of light emitting elements 110*a* and the main diffusion unit 181 to achieve uniform illumination over the entire surface of the main diffusion unit 181.

To this end, the auxiliary diffusion unit 182 may be disposed over the light source unit 110 including the plurality of light emitting elements 110*a* to diffusely transmit the light generated by the plurality of light emitting elements 110*a* to the main diffusion unit 181. The auxiliary diffusion unit 182 may be implemented with an optical material such as a lens that can diffuse the light emitted from the light emitting element 110*a*.

The auxiliary diffusion unit 182 may include a plurality of hemispherical lenses 182*a* corresponding to each of the plurality of light emitting elements 110*a* as illustrated in FIG. 7. According to an embodiment, the auxiliary diffusion unit 182 may be implemented in a form different from the example illustrated in FIG. 7.

A magnetic material fixing frame 186 may have a mounting groove in which the third magnetic material M3 and the fourth magnetic material M4 can be mounted. The third magnetic material M3 and the fourth magnetic material M4 mounted in the magnetic material fixing frame 186 may be fixedly disposed in the lower portion and at the lower center of the first body 180 respectively.

Figure 8:
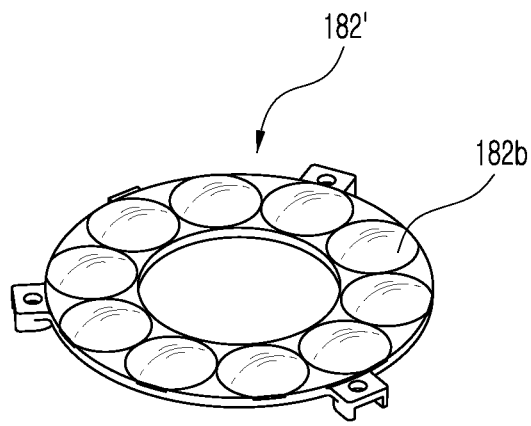
FIGS. 8 and 9 are diagrams illustrating an auxiliary diffusion unit according to another embodiment of the present invention.
Figure 9:
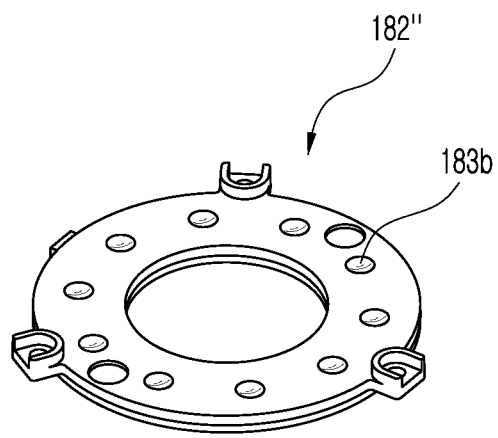

FIGS. 8 and 9 are diagrams illustrating an auxiliary diffusion unit according to another embodiment of the present invention.

Referring to FIG. 8, instead of the auxiliary diffusion unit 182 illustrated in FIG. 7, an auxiliary diffusion unit 182' having a plurality of convex surfaces 182*b* formed thereon may be used. A lower portion of the auxiliary diffusion unit 182' may be flat, or formed with a plurality of concave surfaces as illustrated in FIG. 9.

Referring to FIG. 9, instead of the auxiliary diffusion unit 182, an auxiliary diffusion unit 182" having a plurality of concave surfaces 182*c* formed on the lower portion may be used. An upper portion of the auxiliary diffusion unit 182" may be flat, or formed with a plurality of convex surfaces as illustrated in FIG. 8.

Figure 10A:
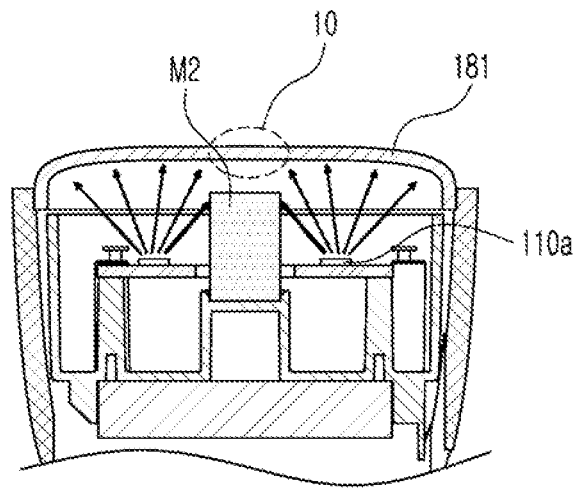
FIGS. 10A and 10B are diagrams provided to describe the function of the auxiliary diffusion unit according to an embodiment of the present invention.
Figure 10B:
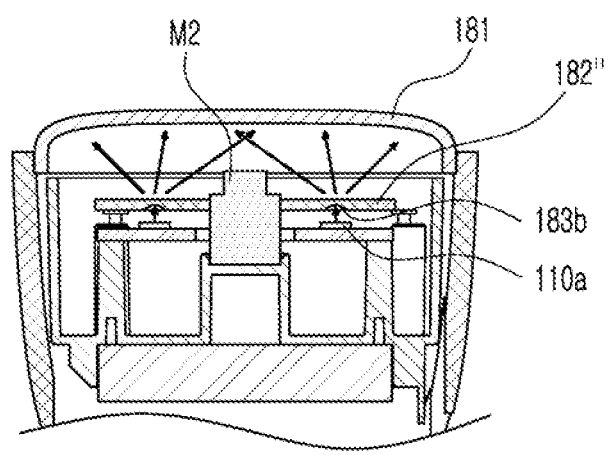

FIG. 10A and FIG. 10B are diagrams provided to describe the function of the auxiliary diffusion unit according to an embodiment of the present invention.

FIG. 10A illustrates an example in which an auxiliary diffusion unit is not provided. The light generated from the light emitting element 110*a* may be blocked by the second magnetic material M2, resulting in a shaded portion 10 in the center of the main diffusion unit 181.

FIG. 10B illustrates an example in which the lighting device is provided with an auxiliary diffusion unit. The auxiliary diffusion unit 182, 182', and 182" may serve to prevent the light generated from the plurality of light emitting elements 110*a* from being blocked by the second magnetic material M2 and forming a shadow in the center of the main diffusion unit 181. FIGS. 10A and 10B illustrate, by way of example, the auxiliary diffusion unit 182" having a plurality of concave surfaces 183*b* formed thereon. Meanwhile, by forming the second magnetic material M2 with its upper portion narrower in width than the lower portion as illustrated in FIG. 10B, it is possible to more effectively prevent a shadow from occurring in the center of the main diffusion unit 181.

At least one of the lower surface of the main diffusion unit 181 and the upper surface of the auxiliary diffusion units 182, 182', and 182" may form a corrosion surface. The corrosion surface may be formed by a method such as etching, sand blasting, or the like. For example, the corrosion surface may be formed by eroding the lower surface of the main diffusion unit 181 or the upper surface of the auxiliary diffusion unit 182, 182', and 182" through chemical treatment. Alternatively, the corrosion surface may be formed by propelling fine powder on the lower surface of the main diffusion unit 181 or the upper surface of the auxiliary diffusion unit 182, 182', and 182" to roughen the surface. The corrosion surface scatters light and thus helps to implement uniform illuminance over the entire surface of the main diffusion unit 181.

Referring to FIGS. 6 and 7, the light source unit 110 may include a plurality of light emitting elements 110*a* and a light emitting element mounting portion 110*b*. The plurality of light emitting elements 110*a* may be mounted on the light emitting element mounting portion 110*b*.

The frame 183 may include a magnetic material insertion portion 183*a* formed in the center to receive the second magnetic material M2 to be fixedly inserted therein, and may be inserted and coupled to the inner space of the first body 180.

The light emitting element mounting portion 110*b* may be coupled to the frame 183 such that the magnetic material insertion portion 183*a* is passed therethrough. To this end, the light emitting element mounting portion 110*b* may have a hole formed in the center, through which the magnetic material insertion portion 183*a* is passed.

The power supply unit 160 and the main board 184 may be disposed under the frame 183.

Electronic components such as the control unit 120, the sensor unit 130, the communication unit 150, and the like may be mounted on the main board 184.

The light emitting element 110*a*, the control unit 120, the sensor unit 130, the communication unit 150, and the like may be operated by the power supplied from the power supply unit 160, and may be connected by power lines, signal lines, and the like for transmitting power and control signals.

The third magnetic material M3 and the fourth magnetic material M4, mounted on the magnetic material fixing frame 186, may be respectively disposed on the lower portion and the central lower portion of the first body 180.

Figure 11:
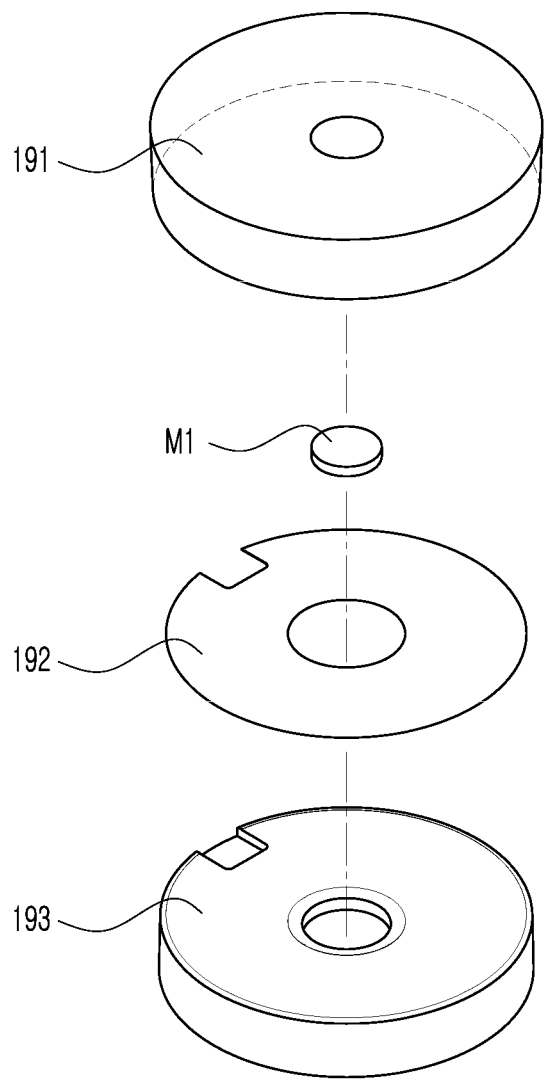
FIG. 11 is an exploded view illustrating components of a second body according to an embodiment of the present invention.

FIG. 11 is an exploded view illustrating components of the second body according to an embodiment of the present invention.

Referring to FIG. 11, the second body 190 may include a cover case 191, a first magnetic material M1, an adhesive film 192, and a silicone rubber 193.

The silicone rubber 193 has an insertion groove into which the first magnetic material M1 is inserted. The adhesive film 192 serves to attach the silicone rubber 193 to the cover case 191. According to an embodiment, another method or material for attaching the silicone rubber 193 to the cover case 191 may be used.

When the lighting device 100 is carried around, the second body 190 is coupled to the first body 180, and the silicone rubber 193 may serve to protect the components mounted on the main diffusion unit 181 and the first body 180. In addition, when the lighting device 100 is in use, it may also serve to prevent the second body 190 from sliding due to friction with the surface on which the second body 190 is placed. The silicone rubber 193 may be formed of an elastic polymer material such as rubber, silicone, or the like.

Figure 12A:
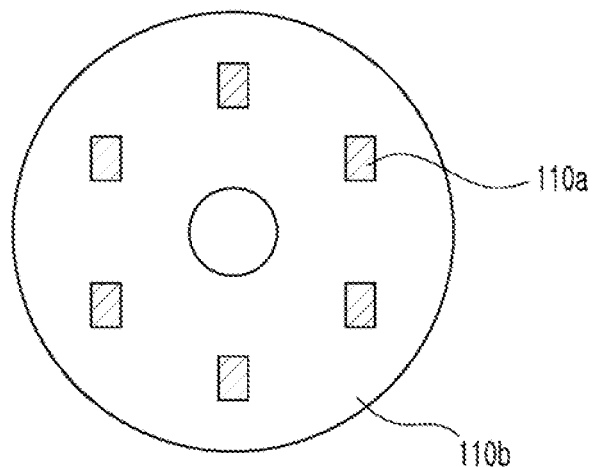
FIGS. 12A and 12B illustrate examples in which light emitting elements are arranged in a light emitting element mounting portion according to an embodiment of the present invention.
Figure 12B:
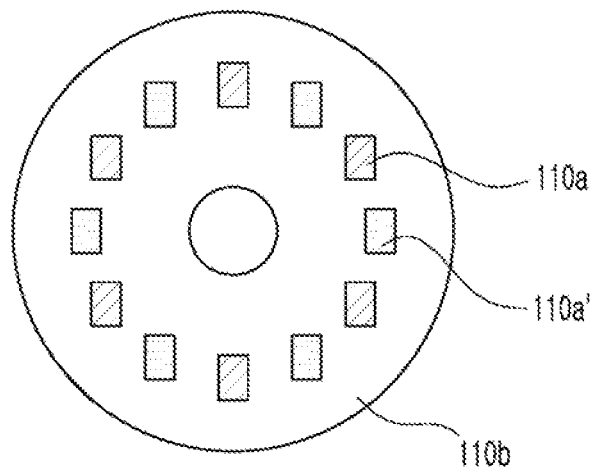

FIGS. 12A and 12B illustrate an example in which light emitting elements are disposed on a light emitting element mounting portion according to an embodiment of the present invention.

Referring to FIGS. 12A and 12B, a plurality of light emitting elements 110a of the same type may be disposed on the light emitting element mounting portion 110b as illustrated in FIG. 12A. Alternatively, a plurality of light emitting elements 110a and 110a' of different types may be alternately disposed on the light emitting element mounting portion 110b as illustrated in FIG. 12B. For example, the light emitting elements 110a may be the awakening LEDs having the light emission spectrum as illustrated in FIG. 2B, and the light emitting elements 110a' may be the relaxation LEDs having the light emission spectrum as illustrated in FIG. 2C.

The light emitting elements 110a and 110a' may be disposed on the light emitting element mounting portion 110b in various ways according to the external shape of the lighting device 100, the presence or absence of the magnetic material M2, and the like. In addition, these elements may be arranged at predetermined intervals for uniform surface brightness of the main diffusion unit 190. In addition, the type or number of the light emitting elements 110a and 110a' to be used may vary according to the purpose of the lighting device 100.

Figure 13A:
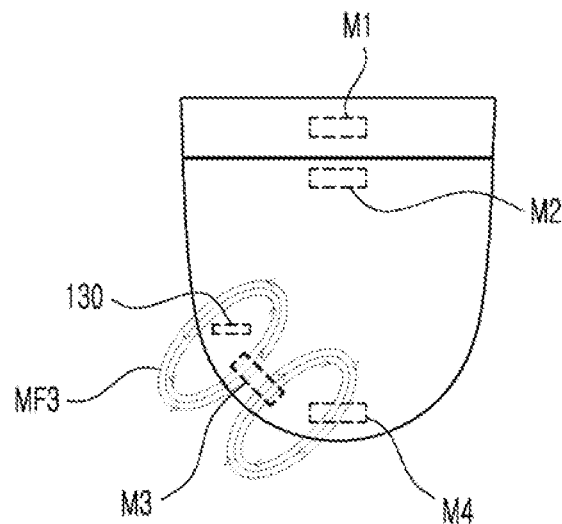
FIGS. 13A, 13B, and 13C are diagrams illustrating relative positions of a magnetic material and a magnetic sensor according to postures and positions of a first body and a second body according to the present invention.
Figure 13B:
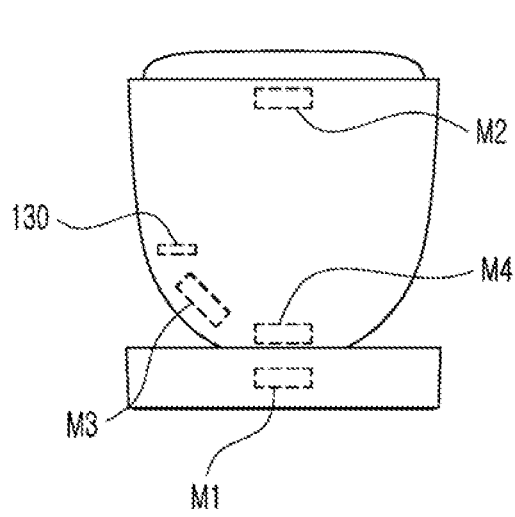
Figure 13C:
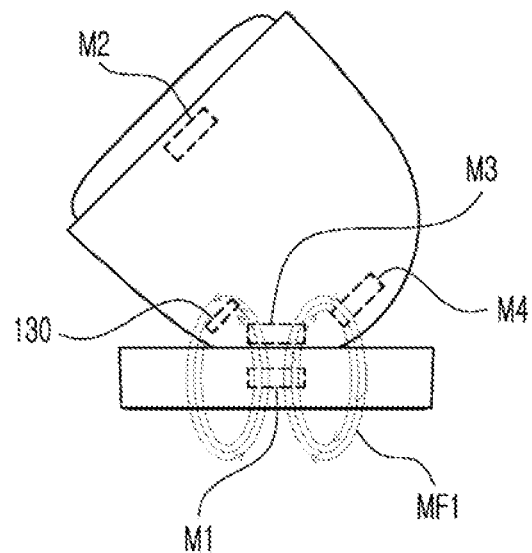

FIGS. 13A, 13B, and 13C are diagrams illustrating relative positions of the magnetic material and the magnetic sensor according to postures and positions of the first body and the second body according to the present invention.

As illustrated in FIG. 13A, with the lower portion of the second body 190 and the upper portion of the first body 180 facing each other, the first body 180 and the second body 190 may be coupled to each other by the magnetic force of the first magnetic material M1 and the second magnetic material M2.

As illustrated in FIG. 13B, when the first body 180 is mounted on the upper portion of the second body 190, the first body 180 may be fixed to the second body 190 in an upright posture by the magnetic force of the first magnetic material M1 and the fourth magnetic material M4.

As illustrated in FIG. 13C, when the first body 180 is mounted on the upper portion of the second body 190, the first body 180 may be fixed to the second body 190 in an inclined posture at a predetermined angle by the magnetic force of the first magnetic material M1 and the third magnetic material M3.

The sensor unit 130 is always spaced apart from the second magnetic material M2 and the fourth magnetic material M4 by a predetermined distance or more. Accordingly, the sensor unit 130 is not turned on by the magnetic field generated by the second magnetic material M2 and the fourth magnetic material M4.

In addition, the sensor unit 130 may be disposed such at the surface of the sensor receiving the magnetic field is shifted from the vertical axis of the third magnetic material M3 by a predetermined angle. As described above, since the sensor unit 130 and the third magnetic material M3 are disposed at the predetermined angle away from each other, the sensor unit 130 may be close to the third magnetic material M3, but not turned on by the magnetic field MF3 generated by the third magnetic material M3.

Meanwhile, the relative positions and postures of the sensor unit 130 and the first magnetic material M1 may vary as illustrated in FIGS. 13A to 13C.

FIGS. 13A and 13B illustrate that the sensor unit 130 and the first magnetic material M1 are spaced apart from each other by a predetermined distance or more. Therefore, the sensor unit 130 is not turned on by the magnetic field generated by the first magnetic material M1.

On the other hand, FIG. 13C illustrates that the magnetic signal by the magnetic field MF1 is input to the sensor unit 130 with a predetermined intensity or more. Accordingly, the sensor unit 130 is turned on by the magnetic field MF1 generated by the first magnetic material M1. In addition, when the sensor unit 130 is turned on, the control unit 120 may drive the light source unit 110 to generate light.

FIGS. 14A, 14B, and 14C are diagrams illustrating the relative positions of the magnetic material and the magnetic sensor according to the postures and the positions of the first body and the second body according to another embodiment of the present invention.

Referring to FIGS. 14A, 14B, and 14C, the lighting device according to another embodiment of the present invention may further include a fifth magnetic material M5 and a sensor unit 130'. In addition, the lighting device may include different types of light emitting elements 110a and 110a' as illustrated in FIG. 12B.

Referring to FIG. 14A, none of the sensor units 130 and 130' is turned on, in which case the control unit 120 turns off the light source unit 110.

FIG. 14B illustrates that only the sensor unit 130 is turned on, in which case the control unit 120 turns on the light emitting element 110a, and turns off the light emitting element 110a'.

FIG. 14C illustrates that only the sensor unit 130' is turned on, in which case the control unit 120 turns off the light emitting element 110a, and turns on the light emitting element 110a'.

According to an embodiment, a sensor other than the magnetic sensor, such as an inertial sensor, an acceleration sensor, or the like may be used for the sensor units 130 and 130'. For example, it is also possible to use the inertial sensor, the acceleration sensor, or the like to sense the posture, movement, or the like of the first body 180. The control unit 120 may control the light emitting operation of the light source unit 110 according to the posture or movement of the first body 180 sensed by the sensor unit 130. In this case, the light source unit 110 may be operated regardless of the user's intention, that is, may be operated according to the posture or movement of the lighting device.

When the lighting device is not in use, the second body 190 is coupled to the upper portion of the first body 180 to cover and protect the main diffusion unit 181. Considering the above function of the second body 190, the second body 190 is also referred to as a "cover part".

The sensor unit 130 and 130' may further include a cover sensing unit, that is, a means for sensing whether or not the cover part 190 is coupled to the upper portion of the first body 180. For example, a physical switch that is pressed upon coupling with the upper portion of the first body 180 may be further provided on the upper portion of the first body 180. When the physical switch is pressed, the control unit 120 may not operate the light source unit 110 regardless of the posture or movement of the first body 180 sensed by the sensor unit 130.

Meanwhile, instead of the physical switch, the lighting device may further include an illuminance sensor under the main diffusion unit 181. The illuminance sensor may sense light coming from the outside through the main diffusion unit 181. Therefore, when the illuminance sensor does not sense the light of a predetermined intensity or more, it may be determined that the cover part 190 is coupled to the upper portion of the first body 180, and accordingly, the control unit 120 may not operate the light source unit 110 regardless of the posture or movement of the first body 180 sensed by the sensor unit 130.

Meanwhile, a magnetic sensor (not illustrated) may be provided under the main diffusion unit 181 instead of a physical switch or an illuminance sensor. When the cover part 190 is coupled to the upper portion of the first body 180, the magnetic sensor provided under the main diffusion unit 181 may be turned on upon sensing a magnetic signal of the first magnetic material M1. When the magnetic sensor provided under the main diffusion unit 181 is turned on, the control unit 120 may not operate the light source unit 110 regardless of the posture or movement of the first body 180 sensed by the sensor unit 130.

The lighting device according to the present invention may include a means for sensing the coupling of the second body 190 to the upper portion of the first body 180 in a manner other than the examples described herein.

Figure 15A:
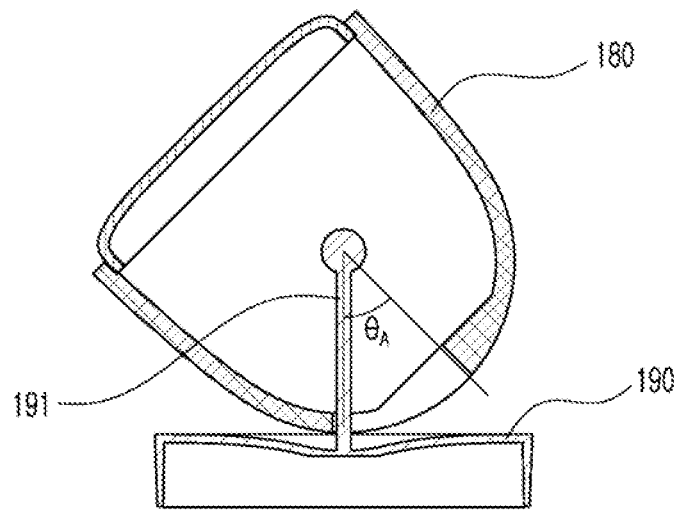
FIGS. 15A, 15B, 16A, 16B, 17A and 17B are diagrams illustrating an external form of a lighting device according to still another embodiment of the present invention.
Figure 15B:
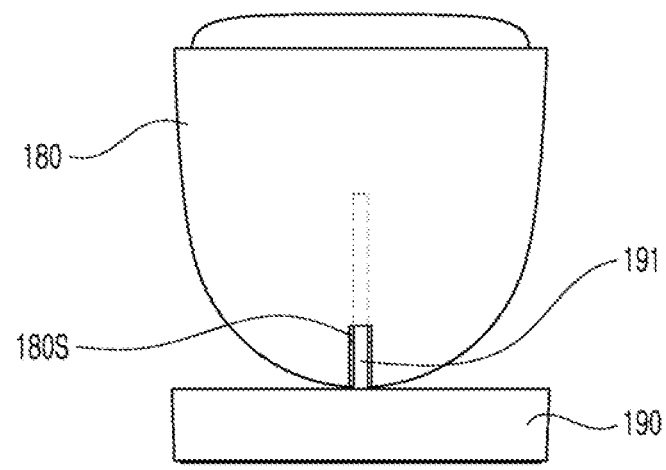

FIGS. 15A and 15B are diagrams illustrating an external form of a lighting device according to still another embodiment of the present invention.

Referring to FIGS. 15A and 15B, the lighting device according to another embodiment of the present invention further includes a support 191 extending upward from the second body 190, in which the first body 180 may be tiltably coupled to the support 191.

The support 191 may protrude upward from the center of the second body 190 and tiltably coupled to the inside of the first body 180.

The first body 180 may be formed with a through slit 180s through which the support 191 is passed. The first body 180 is able to tilt with respect to the support 191 by an angle (OA) corresponding to the range in which the through slit 180s is formed.

Figure 16A:
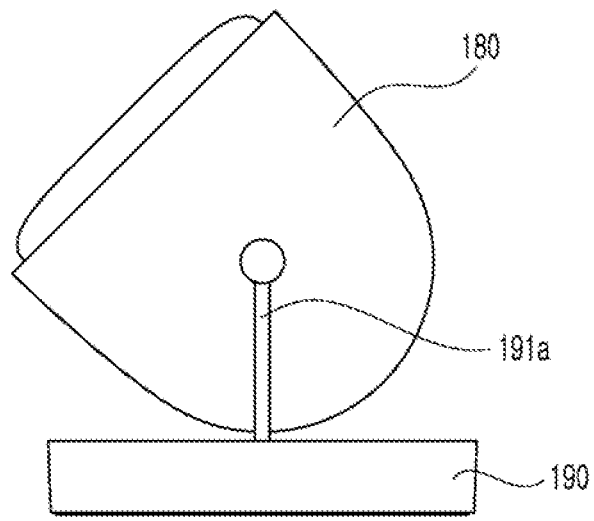
Figure 16B:
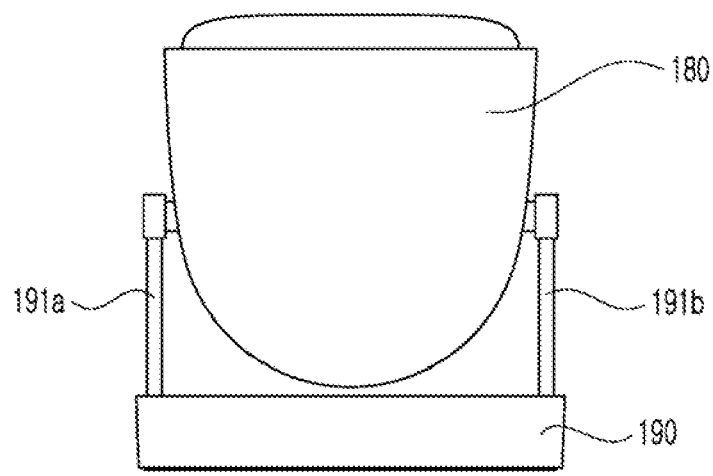

FIGS. 16A and 16B are diagrams illustrating an external form of a lighting device according to still another embodiment of the present invention.

Referring to FIGS. 16A and 16B, the lighting device according to still another embodiment of the present invention further includes a plurality of supports 191a and 191b extending upward from the second body 190, in which the side of the first body 180 may be tiltably coupled to the supports 191a and 191b.

The lighting device may not be provided with a magnetic sensor or a magnetic material in the first body 180 and the second body 190. As described above, the lighting device may include the inertial sensor, the acceleration sensor, and the like to sense the relative posture and/or position of the first body 180 with respect to the second body 190.

Figure 17A:
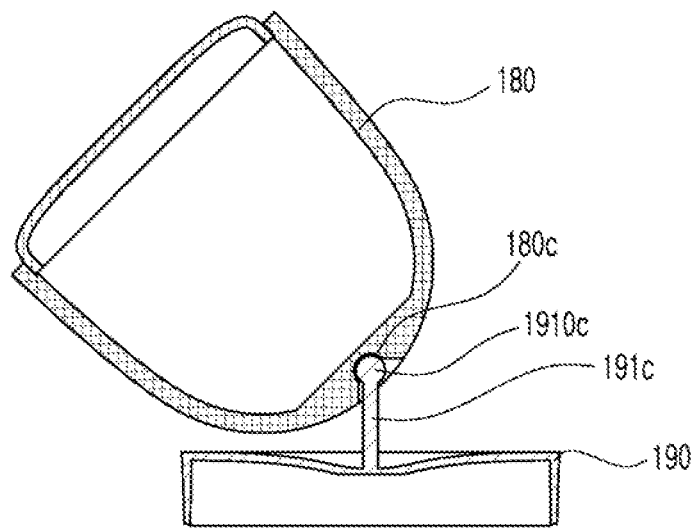
Figure 17B:
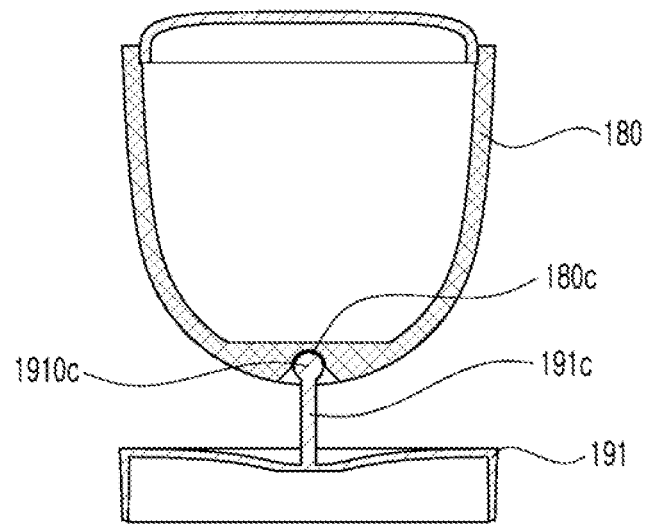

FIGS. 17A and 17B are diagrams illustrating an external form of a lighting device according to still another embodiment of the present invention.

Referring to FIGS. 17A and 17B, the lighting device according to still another embodiment of the present invention may further include a support 191c. The support 191c may protrude upward from the center of the second body 190, and include a spherical sphere 1910c formed at an end of the support 191c.

The sphere 1910c may be rotatably inserted in an insertion hole 180c formed in the lower portion of the first body 180 so as to be rotated in three axes (roll/pitch/yaw). With this structure, the first body 180 may be placed on the second body 190 in a posture desired by the user while being supported by the support 191c. For example, as illustrated in FIG. 17A, the first body 180 may be inclined with respect to the second body 190 at a predetermined angle, or may be in an upright posture as illustrated in FIG. 17B.

The lighting device according to the present invention described with reference to FIGS. 15 to 17 may include the components included in the lighting device 100 described above with reference to FIGS. 1 to 14, except as otherwise explicitly described herein.

The lighting device according to the present invention described above with reference to FIGS. 15 to 17 may not include a magnetic sensor or a magnetic material in the first body 180 and the second body 190. The lighting device may include an inertial sensor, an acceleration sensor, and the like instead of the magnetic sensor to sense the relative posture and/or position of the first body 180 with respect to the second body 190. In addition, the control unit 120 may control the light emitting operation of the light source unit 110 according to the relative posture and/or position of the first body 180 with respect to the second body 190.

Figure 18:
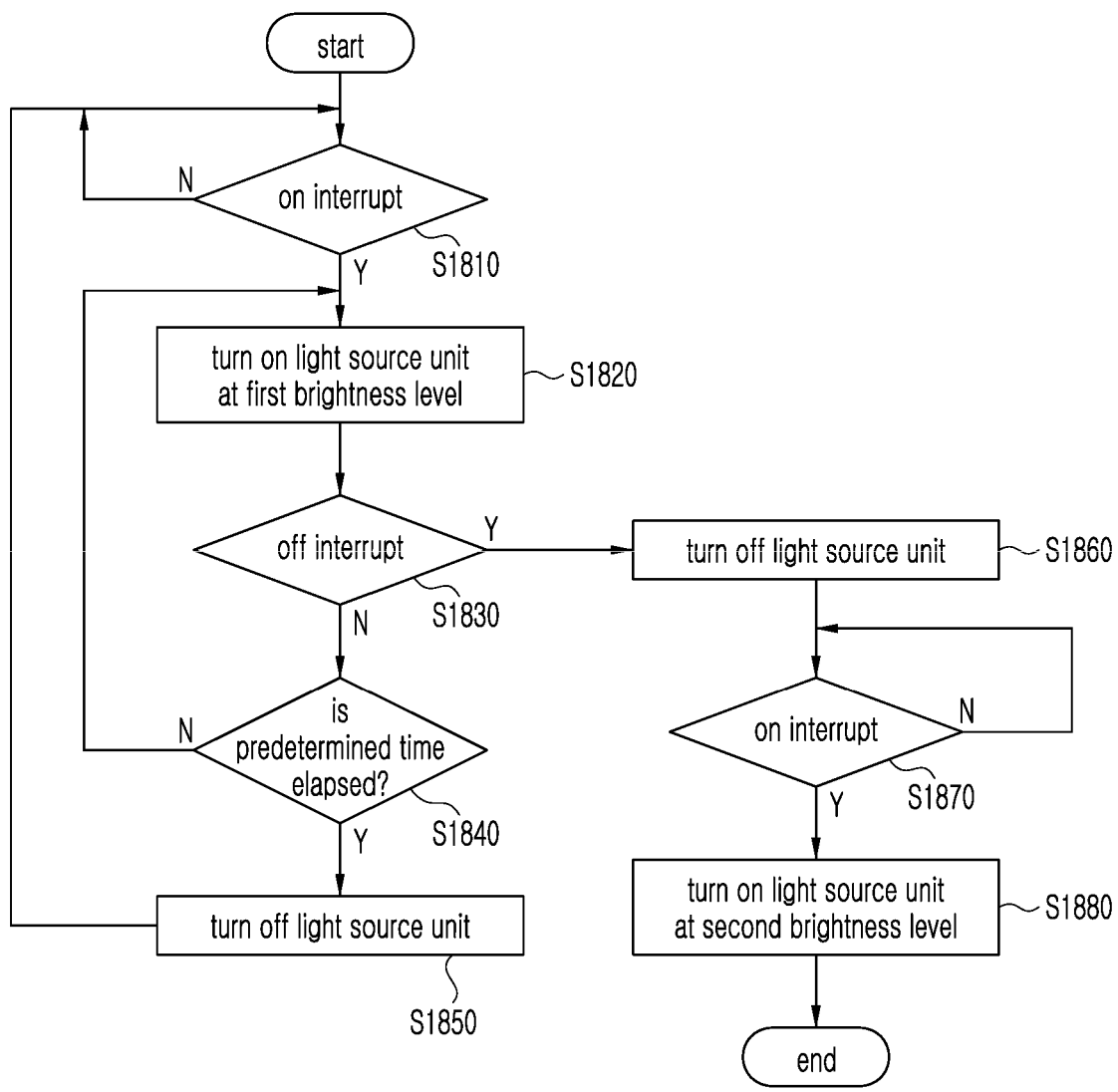
FIG. 18 is a flowchart illustrating a method for controlling a lighting device according to an embodiment of the present invention.

FIG. 18 is a flowchart illustrating a method for controlling a lighting device according to an embodiment of the present invention.

Referring to FIG. 18, first, when an ON interrupt is generated while the light source unit 110 is OFF (S1810—Y), the control unit 120 may turn on the light source unit 110 to generate light at a first brightness level (S1820). For example, as illustrated in FIGS. 13C, 15A, 16A, and 17A, an ON interrupt may be generated when the first body 180 is inclined with respect to the second body 190. Of course, according to an embodiment, it may also be possible that an ON interrupt is generated by other conditions.

Then, while the light source unit 110 is ON, when an OFF interrupt is generated before a predetermined time elapses (S1830—Y), the control unit 120 may turn off the light source unit 110 (S1860). For example, when the first body 180 is erected in the upright posture as illustrated in FIGS. 13B, 15B, 16B, and 17B, an OFF interrupt may be generated. Of course, according to an embodiment, it may also be possible that an OFF interrupt is generated by other conditions.

When the predetermined time elapses while the light source unit 110 is ON (51840—Y), the control unit 120 may turn off the light source unit 110 (S1850). In this case, the predetermined time may be a default value of the lighting device 100 or a value arbitrarily set by the user. Alternatively, the predetermined time may be a value that is automatically set and changed according to circumstances of the user, and the like, by a learning model included in the control unit 120.

If an ON interrupt is generated after step S1850 (S1810—Y), the control unit 120 may turn on the light source unit 110 to generate light at the first brightness level again (S1820). If the lighting device 100 is continuously used at a specific brightness level for a predetermined time, it may be determined that the user prefers the corresponding brightness level. Therefore, when the lighting device 100 is used again, the lighting device 100 may generate light again at the same brightness level as before.

Conversely, if an ON interrupt is generated after step S1860 (S1870—Y), the control unit 120 may turn on the light source unit 110 to generate light at the second brightness level (S1880). In this case, since the use of the lighting device 100 is stopped before the predetermined time is elapsed, the lighting device 100 may generate light at a brightness level different from the previous brightness level.

Embodiments of the present invention may also be implemented in the form of a recording medium including instructions executable by a computer, such as a program module executed by a computer. A computer-readable medium may be any available medium that is accessible by a computer and includes a volatile medium, a nonvolatile medium, a removable medium, a non-removable medium, and so on. In addition, the computer-readable medium may include a computer storage medium and a communication media. The computer storage medium includes a volatile medium, a non-volatile medium, a removable medium, a non-removable medium, or the like, which may be implemented with any method or technology for storage of information such as computer readable instructions, data structures, program modules or other data. The communication medium may typically include computer readable instructions, data structures, or other data in a modulated data signal, such as program modules.

In addition, in the present invention, the "unit", "part" or "portion" may refer to a hardware component such as a processor or a circuit, and/or to a software component executed by the hardware component such as a processor.

The foregoing description of the present invention is for illustrative purposes only, and those of ordinary skill in the art to which the present invention pertains will be able to understand that modifications to other specific forms can be easily performed without changing the technical spirit or essential features of the present invention. Therefore, it should be understood that the embodiments described above are illustrative and non-limiting in all respects. For example, each component described as a single type may be implemented in a distributed manner, and similarly, components described as being distributed may also be implemented in a combined form.

While the scope of the present invention is represented by the claims accompanying below, the meaning and the scope of the claims, and all the modifications or modified forms that can be derived from the equivalent concepts will have to be interpreted as falling into the scope of the present invention.

The invention claimed is:

1. A lighting device comprising:
a light source unit including one or more light emitting elements;
a first body to which the light source unit is mounted;
a second body;
a sensor unit configured to sense at least one of a relative posture and a relative position of the first body with respect to the second body; and
a control unit configured to control a light emitting operation of the light source unit on the basis of at least one of the relative posture and the relative position of the first body;
wherein the second body includes a first magnetic material at a predetermined position,
the sensor unit includes a magnetic sensor mounted at a predetermined position in the first body, and
at least one of the relative posture and the relative position of the first body is determined on the basis of a magnetic signal sensed at the magnetic sensor;
wherein the first body has an open upper portion, an inner space defined therein, and an outer circumferential surface with a gradually decreasing diameter in a downward direction; and
wherein the first body includes at least one of: a second magnetic material disposed in an upper center portion of the first body; a third magnetic material disposed in a lower portion of the first body at a predetermined distance from a central axis of the first body; and a fourth magnetic material disposed in a lower center portion of the first body, and
the second body includes the first magnetic material in a center of the second body.

2. The lighting device of claim 1, wherein the one or more light emitting elements includes one or more first light emitting elements emitting light having a first characteristic, and one or more second light emitting elements having a second characteristic.

3. The lighting device of claim 2, wherein the control unit selectively turns on and off the one or more first light emitting elements and the one or more second light emitting elements on the basis of at least one of the relative posture and the relative position of the first body,
wherein the first light emitting elements have a first spectrum, and the second light emitting elements have a second spectrum.

4. The lighting device of claim 3, wherein the first spectrum has a greater light intensity in a wavelength band of 450 to 490 nm than in other wavelength bands, and the second spectrum has a lesser light intensity in the wavelength band of 450 to 490 nm than the first spectrum.

5. The lighting device of claim 1, wherein, with the first body being mounted on an upper portion of the second body, the first body is fixed to the second body in an inclined posture at a predetermined angle by a magnetic force of the first magnetic material and the third magnetic material.

6. The lighting device of claim 1, wherein, with the first body being mounted on the upper portion of the second body, the first body is fixed to the second body in an upright posture by a magnetic force of the first magnetic material and the fourth magnetic material.

7. The lighting device of claim 1, wherein the magnetic sensor is disposed in a lower portion of the first body at a predetermined distance from an upper portion of the third magnetic material.

8. The lighting device of claim 1, wherein, with the first body being fixed to the second body in an inclined posture at a predetermined angle by the magnetic force of the first magnetic material and the third magnetic material, the magnetic sensor is turned on by a magnetic field generated by the first magnetic material.

9. A lighting device comprising:
a light source unit including one or more light emitting elements;
a first body to which the light source unit is mounted;
a second body;
a sensor unit configured to sense at least one of a relative posture and a relative position of the first body with respect to the second body; and
a control unit configured to control a light emitting operation of the light source unit on the basis of at least one of the relative posture and the relative position of the first body;
wherein the first body includes an inner space defined therein, and an open upper portion,
the light source unit includes a plurality of light emitting elements arranged in the inner space at a predetermined distance from a central axis of the first body, and
the lighting device further includes a main diffusion unit configured to cover the open upper portion of the first body and to diffusely transmit light generated by the light source unit;
wherein the lighting device further includes an auxiliary diffusion unit disposed over the plurality of light emitting elements to diffusely transmit light generated by the plurality of light emitting elements to the main diffusion unit;
wherein the auxiliary diffusion unit includes a lens including, formed on a lower portion thereof, a plurality of concave surfaces corresponding to each of the plurality of light emitting elements, and
wherein the auxiliary diffusion unit includes a plurality of lenses corresponding to each of the plurality of light emitting elements, and
the plurality of lenses include a concave surface formed on a lower portion or a convex surface formed on an upper portion.

10. The lighting device of claim 1, wherein the first body and the second body are coupled to each other by a magnetic force of the first magnetic material and the second magnetic material, with a lower portion of the second body and an upper portion of the first body facing each other.

11. The lighting device of claim 9, wherein a corrosion surface is formed on at least one of a lower surface of the main diffusion unit and an upper surface of the auxiliary diffusion unit.

12. A lighting device comprising:
a light source unit including one or more light emitting elements;
a first body to which the light source unit is mounted;
a second body;
a sensor unit configured to sense at least one of a relative posture and a relative position of the first body with respect to the second body; and
a control unit configured to control a light emitting operation of the light source unit on the basis of at least one of the relative posture and the relative position of the first body;
wherein the first body includes an inner space defined therein, and an open upper portion,
the light source unit includes a plurality of light emitting elements arranged in the inner space at a predetermined distance from a central axis of the first body, and
the lighting device further includes a main diffusion unit configured to cover the open upper portion of the first body and to diffusely transmit light generated by the light source unit; and
wherein the lighting device further includes an auxiliary diffusion unit disposed over the plurality of light emitting elements to diffusely transmit light generated by the plurality of light emitting elements to the main diffusion unit;
the lighting device further comprising a magnetic material disposed in an upper center portion of the inner space defined in the first body,
wherein the magnetic material is positioned below the main diffusion unit, and at least a portion of the magnetic material may be positioned above the auxiliary diffusion unit.

13. The lighting device of claim 12, further comprising:
a frame including a magnetic material insertion portion formed in the center to receive the magnetic material that is inserted and fixed therein; and
a light emitting element mounting portion which is coupled to the frame such that the magnetic material is passed therethrough, and on which the plurality of light emitting elements are mounted.

14. The lighting device of claim 13, wherein the magnetic material is positioned above the light emitting element mounting portion, wherein the magnetic material is formed such that its upper portion is narrower in width than its lower portion.

15. A lighting device comprising:
a light source unit (110) including one or more light emitting elements;
a first body (180) to which the light source unit is mounted;
a second body (190);
a sensor unit (130), including a magnetic sensor, configured to sense at least one of a relative posture and a relative position of the first body (180) with respect to the second body (190); and
a control unit (120) configured to control a light emitting operation of the light source (110) unit on the basis of at least one of the relative posture and the relative position of the first body (180);
wherein the second body (190) includes a first magnetic material (M1) in a center of the second body,
wherein the first body (180) includes a third magnetic material (M3) disposed in a lower portion of the first body at a predetermined distance from a central axis of the first body; and a fourth magnetic material (M4) disposed in a lower center portion of the first body,
wherein the magnetic sensor is disposed in a lower portion of the first body at a predetermined distance from an upper portion of the third magnetic material (M3),
wherein the first body (180) is fixed to the second body (190) in an upright posture by a magnetic force of the first magnetic material (M1) and the fourth magnetic material, or the first body (180) is fixed to the second body (190) in an inclined posture at a predetermined angle by the magnetic force of the first magnetic material and the third magnetic material, and
wherein the control unit (120) turns on the light source unit (110) if the magnetic sensor is turned on by a magnetic field generated by the first magnetic material (M1).

* * * * *